(12) United States Patent
Podany et al.

(10) Patent No.: US 7,037,306 B2
(45) Date of Patent: May 2, 2006

(54) SYSTEM FOR CREATING LINEAR LESIONS FOR THE TREATMENT OF ATRIAL FIBRILLATION

(75) Inventors: Vaclav Podany, New Fairfield, CT (US); Rajesh Pendekanti, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 166 days.

(21) Appl. No.: 10/609,692

(22) Filed: Jun. 30, 2003

(65) Prior Publication Data

US 2004/0267167 A1    Dec. 30, 2004

(51) Int. Cl.
*A61B 18/18*    (2006.01)
*A61B 8/14*    (2006.01)

(52) U.S. Cl. .......................... 606/27; 600/459; 600/439; 606/31

(58) Field of Classification Search .................. 606/27, 606/28, 32–34, 37–41, 48–50; 600/437, 600/439, 459, 462; 601/2, 3
See application file for complete search history.

(56) References Cited

U.S. PATENT DOCUMENTS

| | | | |
|---|---|---|---|
| 5,647,871 A | 7/1997 | Levine et al. | |
| 5,676,692 A * | 10/1997 | Sanghvi et al. | 607/98 |
| 6,007,499 A * | 12/1999 | Martin et al. | 601/3 |
| 6,117,101 A * | 9/2000 | Diederich et al. | 604/22 |
| 6,119,041 A | 9/2000 | Pomeranz et al. | |
| 6,235,024 B1 * | 5/2001 | Tu | 606/41 |
| 6,413,254 B1 * | 7/2002 | Hissong et al. | 606/27 |
| 6,488,680 B1 | 12/2002 | Francischelli et al. | |
| 6,605,084 B1 * | 8/2003 | Acker et al. | 606/28 |
| 6,645,202 B1 * | 11/2003 | Pless et al. | 606/41 |
| 6,692,491 B1 | 2/2004 | Phan | |
| 2002/0042610 A1 | 4/2002 | Sliwa, Jr. et al. | |
| 2004/0116921 A1 | 6/2004 | Sherman et al. | |

* cited by examiner

*Primary Examiner*—Michael Peffley

(57) ABSTRACT

A system for forming linear lesions in tissue, the system comprising a control unit having an ultrasound vibration driving section, and an ultrasonic applicator operatively connected to the control unit. The ultrasonic applicator comprises an ultrasonic transducer having an acoustic window, and an ultrasonic vibratory element, the ultrasonic vibratory element having a convergent shape with a focus located in the direction of the acoustic window. An air gap is adjacent to the ultrasonic vibratory element in an opposite direction from the focal point. The system further comprises means for controlling the depth of the lesion formed in the tissue.

10 Claims, 6 Drawing Sheets

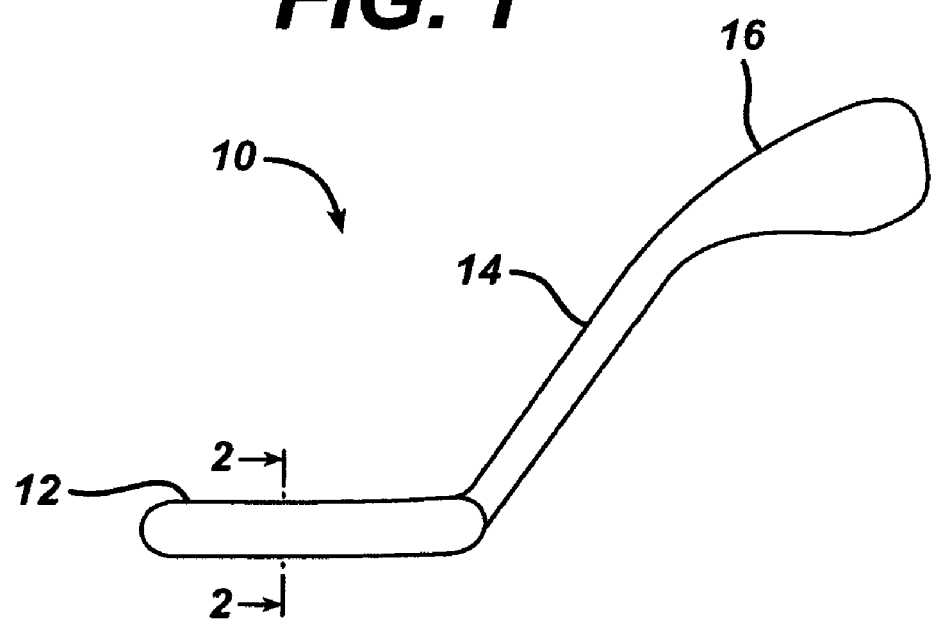
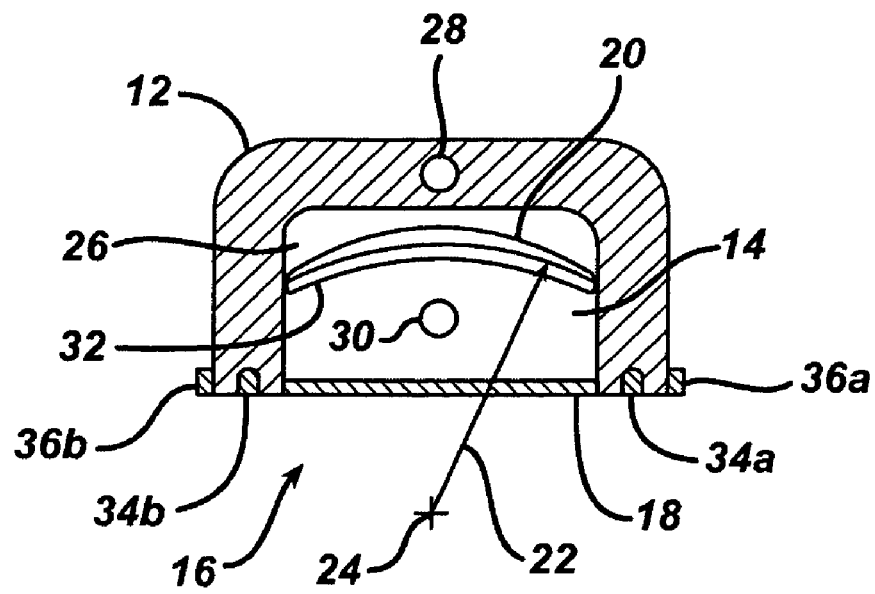

SYSTEM FOR CREATING LINEAR LESIONS FOR THE TREATMENT OF ATRIAL FIBRILLATION

BACKGROUND OF THE INVENTION

1. Field of Invention

The invention relates generally to the field of surgical instrumentation, and more particularly, to an ultrasonic applicator for creating linear lesions in living tissue.

2. Description of Related Art

Atrial fibrillation is the most common form of cardiac arrhythmia (irregular heartbeat). Irregular heartbeats are caused by abnormal electrical activity of the heart. In atrial fibrillation, the atria, the upper chambers of the heart, beat irregularly and rapidly. The erratic electrical signals may also cause ventricles, the lower chambers of the heart, to beat irregularly and rapidly. This can affect blood flow to the heart muscle and to the rest of the body.

Treatment for includes medication, or cardioversion, electrical stimulation of the heart, to restore normal sinus rhythm. Patients who do not respond to these treatments may be indicated for surgery, including catheter ablation, or more recently developed MAZE techniques.

In a traditional MAZE procedure, incisions are made in a predetermined pattern in the inter wall of the atria, which are then sutured together. Scar tissue that forms at the incisions inhibits the conduction of electrical impulses in the heart tissue that causes the fibrillation. The electrical impulses are directed along, rather than across, the incisions in a maze-like fashion that leads them to the lower ventricles of the heart.

Although generally effective, the procedure implicates the risks associated with major heart surgery. The procedure generally takes several hours, during which time the patient must receive cardiopulmonary life support. Even if successful, the procedure is highly invasive and traumatic, with full recovery taking up to six months. Additionally, the procedure requires exacting skill on the part of the surgeon.

BRIEF SUMMARY OF THE INVENTION

Therefore, an apparatus able to produce lesions of scar tissue in the wall of the heart muscle quickly, reliably, and without the need to enter the heart muscle or even stop the beating heart would therefore be highly desirable. It would also be desirable to form the lesions quickly, while minimizing damage to tissue surrounding the lesions.

Provided by the present invention is a system for forming linear lesions in tissue, the system comprising a control unit having an ultrasonic generator, and an ultrasonic applicator operatively connected to the control unit. The ultrasonic applicator comprises an ultrasonic transducer having an acoustic window, and an ultrasonic vibratory element, the ultrasonic vibratory element having a shape focusing ultrasound toward a focus located in the direction of the acoustic window. An air gap is adjacent to the ultrasonic vibratory element in an opposite direction from the focal point. The system further comprises means for controlling the depth of the lesion formed in the tissue.

BRIEF DESCRIPTION OF THE DRAWINGS

These and other features, benefits and advantages of the present invention will become apparent with reference to the following specification and accompanying drawing, in which like reference numerals indicate like features across the several views.

FIG. 1 illustrates an ultrasonic applicator according to a first embodiment of the present invention;

FIG. 2 illustrates a cross-section of the transducer head of the ultrasonic applicator, taken along the section line 2—2 of FIG. 1;

DETAILED DESCRIPTION OF THE INVENTION

Figure 3:
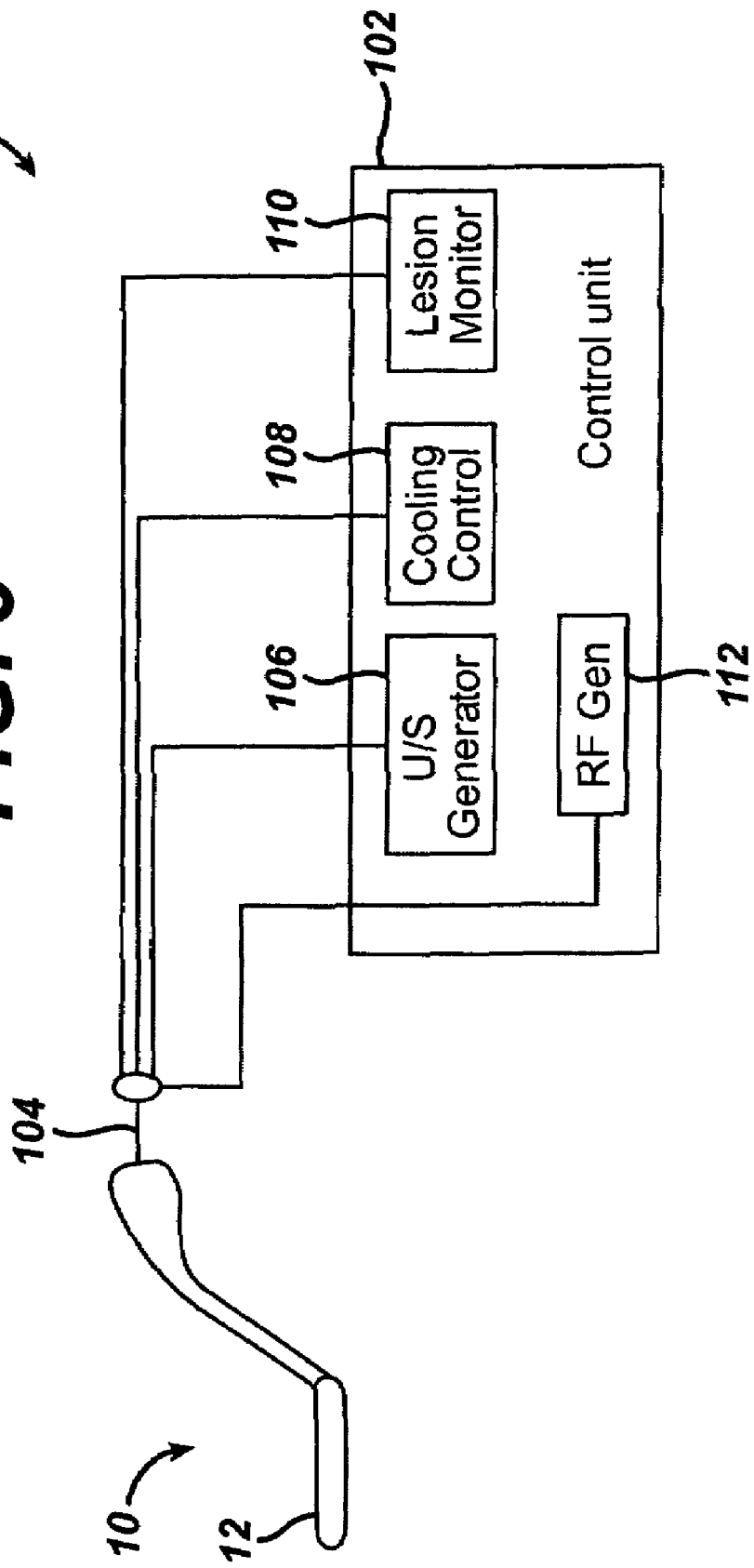
FIG. 3 is a schematic illustration of a system for creating linear lesions according to the present invention.

Referring now to FIG. 1, illustrates is an ultrasonic applicator, generally 10, according to the present invention. Ultrasonic applicator 10 has a transducer head 12, a shaft 14, and a handle 16, by which the applicator 10 may be manipulated. Not shown in FIG. 1 are passages and cables by which power and cooling fluid, retrospectively, are supplied to the applicator 10. These passages and cables may be either internal or external to the shaft 14.

Turning now to FIG. 2, a cross section of transducer head 12 is shown, taken along line 2—2 of FIG. 1. Transducer head 12 is formed with a cavity 14 therein which is open to an acoustic window 16. The cavity 14 is sealed across the acoustic window 16 by a membrane 18. Membrane 18 is selected to have a low acoustic impedance and low coefficient of acoustic absorption, for acoustic transparency, such as films of Ultem, PET, or Styron. In one embodiment, 0.001" thickness PEEK was used.

Located within cavity 14 is the ultrasonic vibratory element, in this embodiment a piezoelectric crystal 20. Piezoelectric crystal 20 has a curvature illustrated by radius 22 and converges at a focus 24 located in the direction of the acoustic window 16. The focal length may be varied, and was set to 0.25" in one exemplary embodiment. Alternately, the transducer head 14 may be provided with a plurality of vibratory elements, either curved or flat, which form some angle with respect to one another. In either case, the ultrasonic energy will converge at some focus.

Provided in a direction opposite the focal point 24 and acoustic window 16 and adjacent the crystal 20 is an air gap 26. The air gap 26 acts as an acoustic mirror to reflect all acoustic energy from the adjacent side of the crystal 20 downward towards the acoustic window 16.

Also provided in the transducer head 12 are cooling passages 28 and 30. These cooling passages 28, 30 allow for the supply and removal of cooling fluid to and from the transducer head 12. The cooling fluid can include, but is not limited to, degassed water or saline. The cooling fluid also provides a coupling path for the ultrasonic energy. The flow of cooling fluid is determined primarily by the energy losses in crystal 20.

In order to further enhance efficiency piezoelectric crystal 20 may be provided with an impedance matching coating 32 on the side of the crystal 20 that faces the acoustic window 16. The coating 32 is shown in exaggerated thickness for illustration, and is typically on the order of one-quarter (¼) of the wavelength of the ultrasonic energy provided by the crystal 20. The selection of material and its impedance will be well known to those skilled in the art, and need not be explained further. The presence of the coating 32 impacts the cooling needs of the transducer 12, and adjustment of the coolant flow, in light of the driving power of the crystal 20, may be necessary.

Provided on either side of the acoustic window 16 are regions of porous material, 34a, 34b. This porous material 34a, 34b may be saturated with an ink, so that as the ultrasonic applicator 10 is used to form lesions in the tissue, the area where lesions have been formed will be marked by the ink. Also provided on either side of the acoustic window 16 are electrodes 36a, 36b. The electrodes 36a, 36b, may be used for pacing, i.e., electrically testing of the effectiveness of the lesions formed in inhibiting the propagation of electrical impulses through the tissue.

Alternately or additionally, electrodes 36a, 36b may be used to provide RF energy to the tissue to enhance the lesions formed by the ultrasonic energy of crystal 20. In combination with ultrasound, the RF energy can be used to form a more complete barrier or transmurality in a wider range of tissue thicknesses. This procedure is explained in more detail in U.S. patent application Ser. No. 10/609,694 entitled Multi-Modality Ablation Device, filed on the same date herewith, which is hereby incorporated by reference for all purposes.

The combination of ultrasound and RF energy comprises one means for controlling the depth of the lesion in the tissue. Other means can be mechanical, for example by adjusting the focal length of the applicator. In one embodiment, the ultrasonic applicator has two crystals arranged within the transducer. By altering either or both of the angle and the distance between the two crystals, the depth of focus is adjusted. This aspect is explained further in U.S. patent application Ser. No. 10/609,693 entitled Ultrasonic Radial Focused Transducer for Pulmonary Vein Ablation, filed on the same date herewith, which is hereby incorporated by reference for all purposes.

Alternately or additionally, the distance between the crystal and the acoustic window may be adjusted by mechanical means, some of which are illustrated in FIGS. 4A through 4G.

Figure 4A:
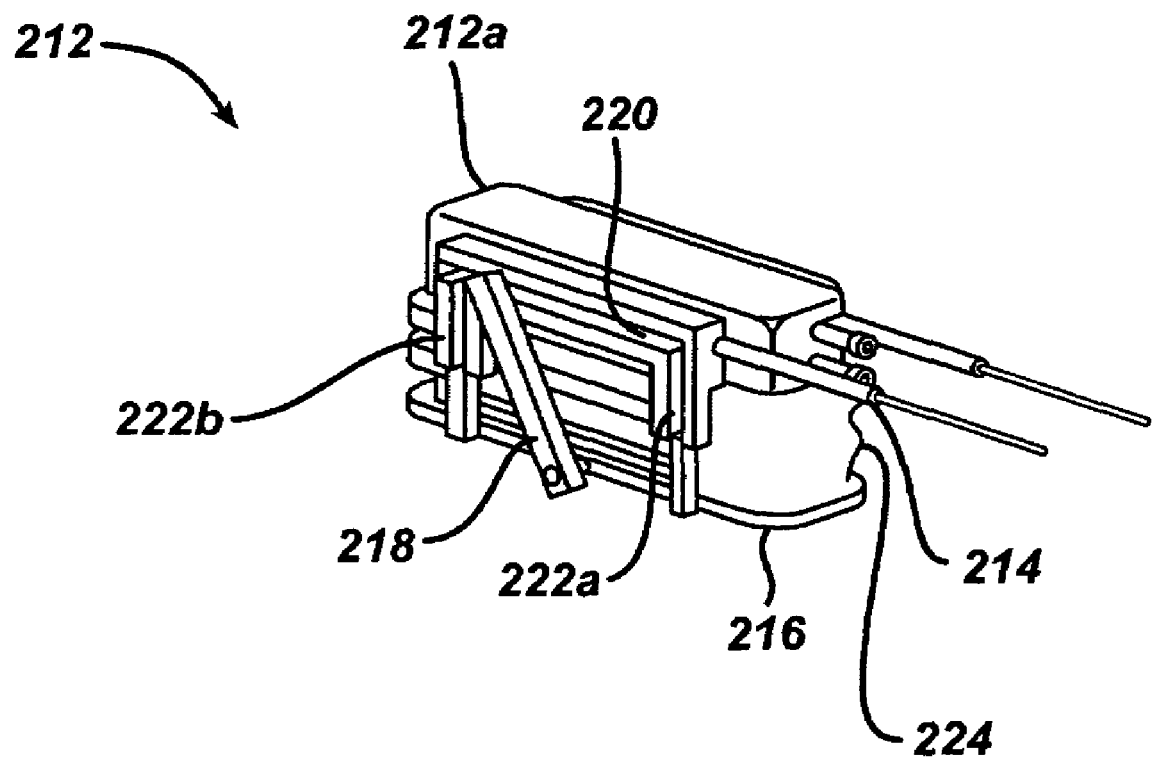
FIGS. 4A through 4G illustrate various embodiments of transducer heads operative to mechanically alter the depth of focus of the ultrasonic energy.

Referring to FIG. 4A, an alternate embodiment of a transducer head, generally 212, is shown. An articulating cable 214 is operatively connected to and longitudinally articulates one end of linkage 218 within slot 220. Thereby, an upper portion 212a of the transducer head 212 moves vertically with respect to the acoustic window 216, guided by slots 222a, 222b. Optionally, the space between upper portion 212a and acoustic window 216 may be enclosed by a flexible skirt 224. A similar cable/linkage/slot arrangement may be provided on an opposite side of transducer head 212.

Figure 4B:
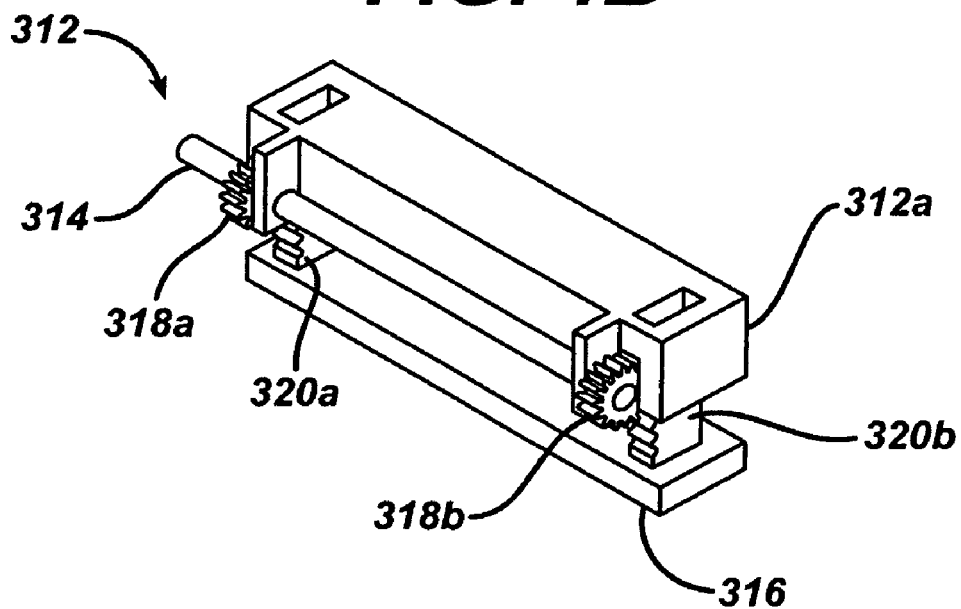

Referring to FIG. 4B, an alternate embodiment of a transducer head, generally 312, is shown. In this embodiment, an articulating cable 314 is operatively connected to pinions 318a, 318b. The articulating cable 312 rotates the pinions 318a, 318b, which are engaged with racks 320a, 320b, respectively. Upper portion 312a of transducer head 312 is thereby moved vertically with respect to acoustic window 316.

Figure 4C:
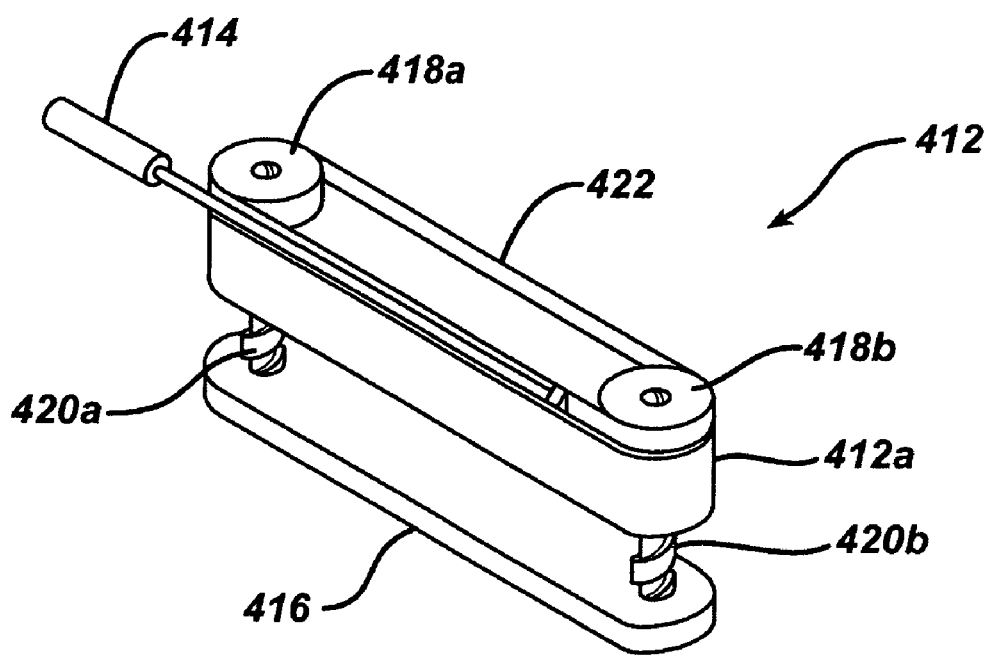

Referring to FIG. 4C, an alternate embodiment of a transducer head, generally 412, is shown. In this embodiment, an articulating cable 414 is operatively connected to band 422. The articulating cable 412 articulates band 422, which is engaged with and synchronously rotates nuts 418a, 418b. Nuts 418a, 418b are engaged with screws 420a, 420b, respectively. As nuts 418a, 418b rotate, upper portion 412a of transducer head 412 is moved vertically with respect to acoustic window 416.

Figure 4D:
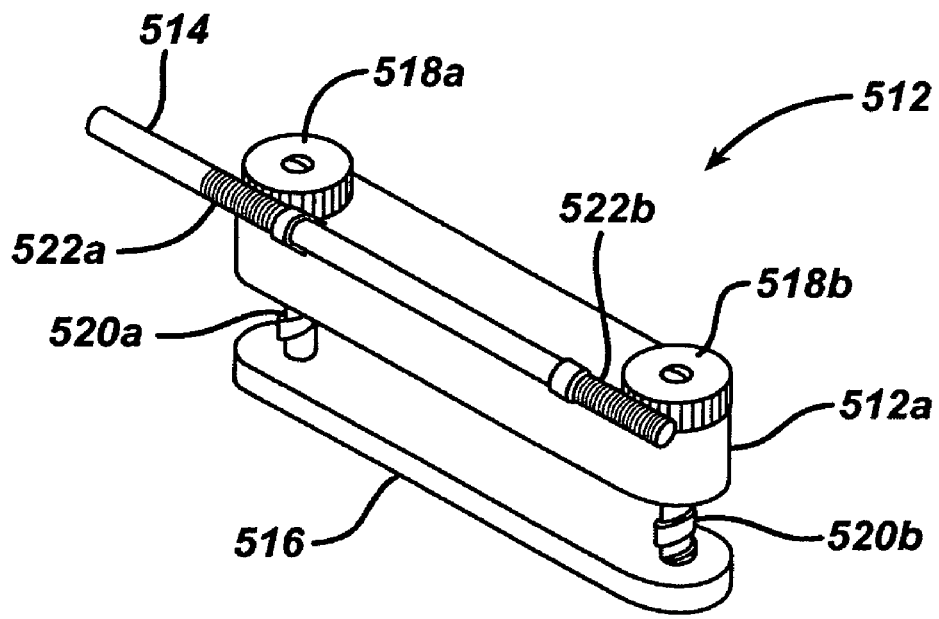

Referring to FIG. 4D, an alternate embodiment of a transducer head, generally 512, is shown. In this embodiment, an articulating cable 514 is operatively connected to worm gears 522a, 5228b. The articulating cable 512 rotates the worm gears 522a, 5228b, which are engaged with nuts 518a, 518b. Nuts 518a, 518b are engaged with screws 520a, 520b, respectively. As nuts 518a, 518b rotate, upper portion 512a of transducer head 512 is moved vertically with respect to acoustic window 516.

Figure 4E:
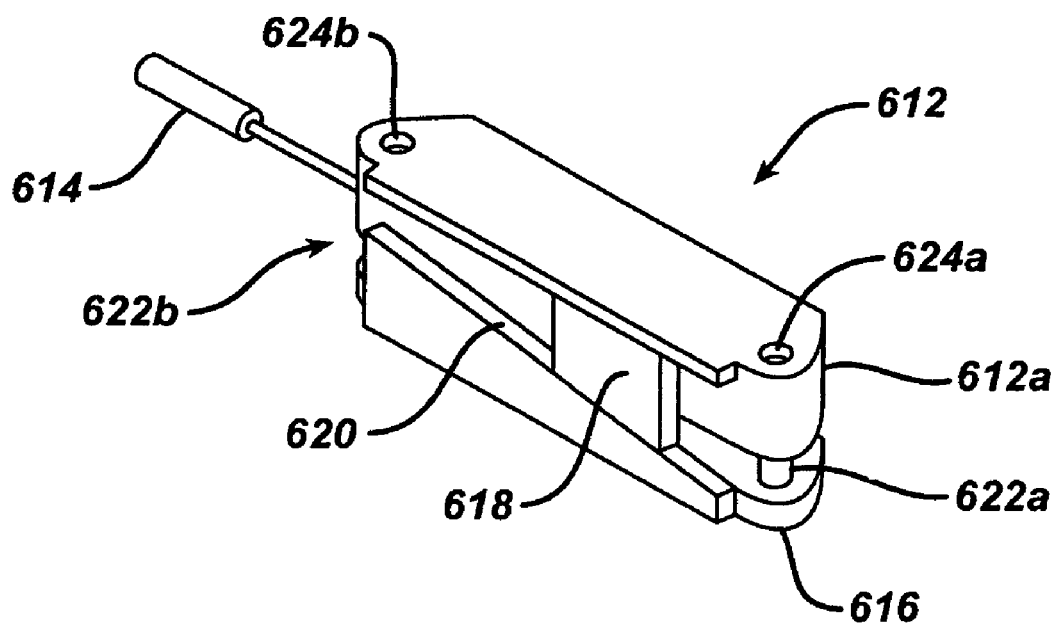

Referring to FIG. 4E, an alternate embodiment of a transducer head, generally 612, is shown. An articulating cable 614 is operatively connected to and longitudinally articulates a wedge 618. Acoustic window 616 may be angled, or may be provided with a sloped flange 620. A track, a sidewall, a flange, a spring or other similar device may be provided to constrain the movement of wedge 618. As wedge 618 moved against flange 618, an upper portion 612a of transducer head 612 moved vertically with respect to acoustic window 616. Upper portion 612a is guided by posts 622a, 622b, and corresponding bores 624a, 624b, respectively. A similar cable/wedge/slope arrangement may be provided on an opposite side of transducer head 612.

Figure 4F:
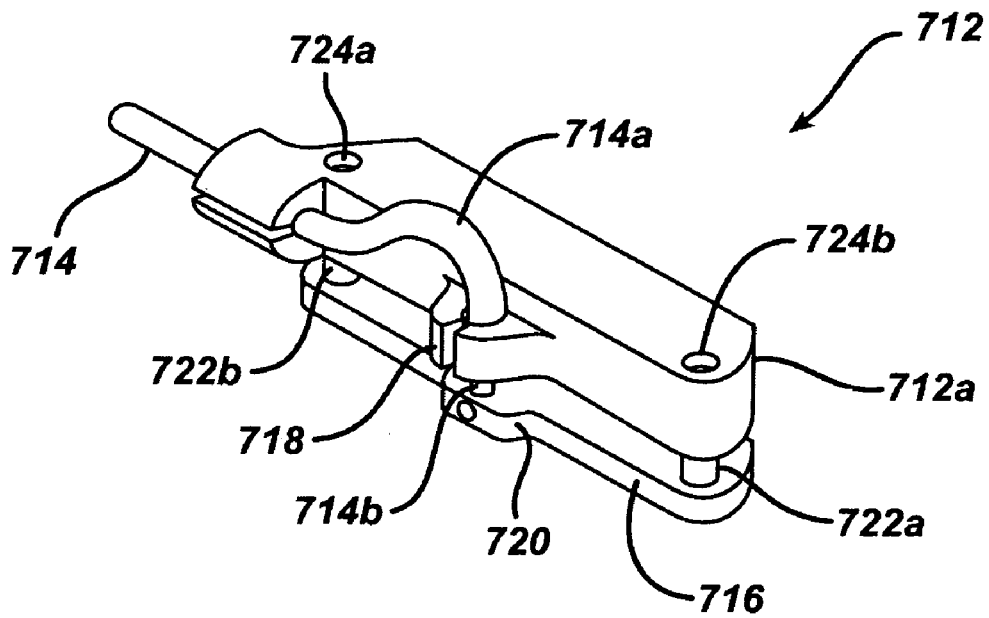

Referring to FIG. 4F, an alternate embodiment of a transducer head, generally 712, is shown. A sheathed cable 714 is operatively connected to transducer head 712. The sheath 714a is connected to an upper portion 712a of the transducer head 712 at bracket 718. The core 714b is connected to the acoustic window 716 at flange 720. As the core 714b moves within the sheath 714a, the upper portion 712a moves vertically with respect to the acoustic window 716. This motion is guided by posts 722a, 722b, and corresponding bores 724a, 724b, respectively. A similar cable/flange arrangement may be provided on an opposite side of transducer head 712.

Figure 4G:
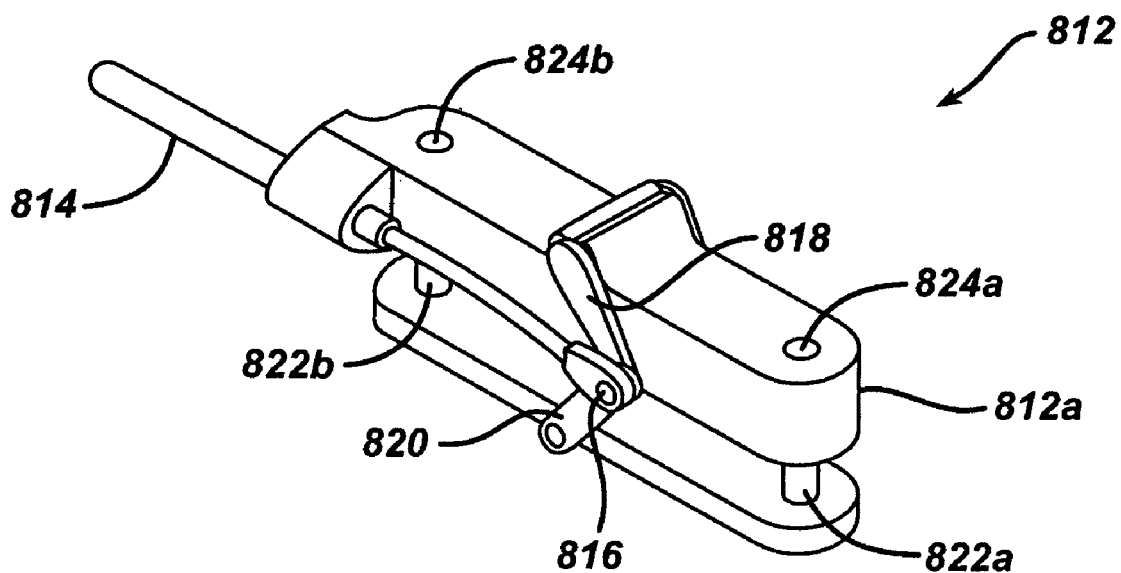

Referring to FIG. 4G, an alternate embodiment of a transducer head, generally 812, is shown. An articulating cable 814 is operatively connected to transducer head 812, and to a common pin 816 joining linkages 818 and 820. As pin 816 moves longitudinally, the upper portion 812a moves vertically with respect to the acoustic window 816. This motion is guided by posts 822a, 822b, and corresponding bores 824a, 824b, respectively. A similar cable/linkage arrangement may be provided on an opposite side of transducer head 812.

Further, selection of the frequency of the ultrasonic wave can be used to control the depth and transmurality of the lesion. Lower frequencies are less absorbed by the tissue and provide deeper penetration. The higher frequencies have higher absorption in the tissue and this provides higher rate of heating but lower penetration. Therefore, by selecting or optimizing the frequency of the crystal 20, the depth of penetration of the ultrasonic energy and the heating rate can be adjusted so that a range of tissue thickness can be ablated, thereby controlling the depth of the lesion. A predetermined target may be established based upon the thickness of the tissue, or a thicker lesion may be formed by adjusting the frequency in process. Control of the ultrasonic frequency comprises yet another means for controlling the depth of the lesion.

Alternately or additionally, either or both of electrodes 36a, 36b, can be made responsive to ultrasound. These can then be used to receive a lower power inspection ultrasound signal, emitted after the lesion is formed to inspect the physical properties of the lesion.

Referring now to FIG. 3, the system, generally 100, for creating linear lesions according to the present invention is shown. The ultrasonic applicator 10 is connected to control unit 102 via a conduit 104. Conduit 104 provides the pathways necessary for electrical, RF, and/or fluid communication with the transducer head 12.

Control unit 102 comprises a ultrasonic generator 106, which supplies power of the appropriate frequency to the crystal 20 for the production of acoustic energy. Control unit 102 also provides a coolant control section 108. Coolant control section 108 can include a pump for the circulation of cooling fluid, sensors for monitoring the temperature of the coolant fluid, and in closed cooling systems, a heat exchanger for expelling heat from the coolant fluid before it is recycled back into the transducer.

Control unit 102 also comprises a lesion monitoring section 110. In combination with electrodes 36a, 36b, once formed, the lesions created can be tested for effectiveness by electrical pacing, discussed supra, or by monitoring the tissue impedance. Additionally or alternately, other methods of monitoring the effectiveness the lesions, including but not limited to, ultrasound imaging, can be employed to verify the suitability of the lesions formed. Additionally, the control unit may comprise an RF generator 112, for applying RF energy to the tissue at the transducer 12, as discussed, supra.

The operation of the system 100, according to the present invention will now be described. Typically, the surgeon will establish access to the epicardium through sternotomy, thoracotomy, or less invasively, by thorascopic port access. The transducer 12 is placed on the surface of the heart where the lesion is to be formed. A trigger switch, which may be located on the shaft 14 of the applicator 10, alternately embodied as a foot pedal for the surgeon, or on the control unit 102, activates the ultrasonic generator 106 to introduce ultrasonic energy to the tissue.

The ultrasonic generator 106 applies electrical energy to the crystal 20 to induce ultrasonic vibration. In one embodiment, the crystal was tuned to 8.72 Mhz and employed a power setting of 60 W. In this exemplary embodiment, acoustic intensity along the focal line including focal point 24 is in a range between 1,000 and 1,500 W/cm$^2$, sufficient to coagulate tissue within a short period of time. In vitro testing indicates the transmural lesion in tissue of typical thickness can be made in about 15 to 30 seconds.

The present invention has been described herein with reference to certain exemplary embodiments. Certain modifications and alterations may be apparent to those skilled in the art without departing from the scope of the present invention. The exemplary embodiments are meant to be illustrative, and not limiting, on the scope of the invention, which is defined by the appended claims.

The invention claimed is:

1. A system for forming linear lesions in tissue, the system comprising:
   a control unit, the control unit having an ultrasonic generator;
   an ultrasonic applicator operatively connected to the control unit, the ultrasonic applicator comprising:
   an ultrasonic transducer having an acoustic window;
   an ultrasonic vibratory element, the ultrasonic vibratory element having a focusing shape with a focus located in the direction of the acoustic window;
   an air gap adjacent to the ultrasonic vibratory element in an opposite direction from the focal point; and
   a porous section adjacent a bottom surface, the porous section capable of holding a supply of marking ink, whereby the location of the lesion is indicated by the marking ink when the transducer is applied to the tissue surface; and the system further comprising means for controlling the depth of the lesion formed in the tissue.

2. The system according to claim 1, wherein the control unit further comprises a cooling section, and the ultrasonic applicator further comprising a passage for communicating cooling fluid from the cooling section to the ultrasonic transducer.

3. The system according to claim 1, wherein the control unit further comprises a lesion monitoring section operatively connected to the ultrasonic transducer.

4. The system according to claim 1, wherein the means for controlling the depth of the lesion formed in the tissue comprises means for applying RF energy to the tissue.

5. The system according to claim 1, wherein the means for controlling the depth of the lesion formed in the tissue comprises means for adjusting the focal length of the ultrasonic applicator.

6. The system according to claim 1, wherein the means for controlling the depth of the lesion formed comprises means for adjusting the distance between the ultrasonic vibratory element and the acoustic window.

7. The system according to claim 1, wherein the control unit further comprises an RF generator operatively connected to the ultrasonic transducer.

8. An ultrasonic applicator comprising:
   an ultrasonic transducer having an acoustic window;
   an ultrasonic vibratory element, the ultrasonic vibratory element having a focusing shape with a focus located in the direction of the acoustic window;
   an air gap adjacent to the piezoelectric crystal in an opposite direction from the focal point;
   a porous section adjacent a bottom surface, the porous section capable of holding a supply of marking ink, whereby the location of the lesion is indicated by the marking ink when the transducer is applied to the tissue surface; and
   means for controlling the depth of the lesion formed in the tissue.

9. The ultrasonic applicator according to claim 8, wherein the means for controlling the depth of the lesion formed comprises means for adjusting the focal length of the ultrasonic applicator.

10. The ultrasonic applicator according to claim 8, wherein the means for controlling the depth of the lesion formed comprises means for adjusting the distance between the ultrasonic vibratory element and the acoustic window.

* * * * *